(12) United States Patent
Blackmon et al.

(10) Patent No.: US 8,960,008 B1
(45) Date of Patent: Feb. 24, 2015

(54) SYSTEM FOR MEASURING VIBRATIONS OCCURING ON A SURFACE

(71) Applicants: Fletcher A Blackmon, Forestdale, MA (US); Lynn T Antonellli, Cranston, RI (US); Anthony J Kalinowski, East Lyme, CT (US)

(72) Inventors: Fletcher A Blackmon, Forestdale, MA (US); Lynn T Antonellli, Cranston, RI (US); Anthony J Kalinowski, East Lyme, CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/927,196

(22) Filed: Jun. 26, 2013

Related U.S. Application Data

(62) Division of application No. 12/902,571, filed on Oct. 12, 2010, now Pat. No. 8,499,637.

(51) Int. Cl.
*G01H 9/00* (2006.01)
(52) U.S. Cl.
CPC ....................................... *G01H 9/00* (2013.01)
USPC ............................................ 73/643; 367/149

(58) Field of Classification Search
USPC .................... 73/643, 655, 657; 367/149, 120; 356/502
See application file for complete search history.

(56) References Cited

U.S. PATENT DOCUMENTS

| | | | |
|---|---|---|---|
| 7,113,447 B1 * | 9/2006 | Matthews et al. | 367/7 |
| 7,251,196 B1 * | 7/2007 | Antonelli et al. | 367/149 |
| 8,599,649 B1 * | 12/2013 | Antonelli et al. | 367/149 |

* cited by examiner

*Primary Examiner* — Laura Martin
*Assistant Examiner* — Rose M Miller
(74) *Attorney, Agent, or Firm* — James M. Kasischke; Michael P. Stanley

(57) ABSTRACT

A device and system is provided for amplifying vibrations resulting from underwater acoustic signals. In operation, a laser interrogation beam is directed along an axis at the retro-reflector device and is responsive to reflections directed along the axis of the interrogation beam. The retro-reflector device reflects a signal back to a source and a tracking signal superimposed on an interrogation beam enables continuous sensing of the reflected signal to reduce signal dropout. A glint tracker is provided for steering the tracking beam on the surface. A tracker system superimposes the tracking and interrogation beams and is responsive to reflected glints in order to establish a directional location. An interferometer responsive to the reflected interrogation beam produces an interference signal for enabling continuous measurement of surface vibrations.

1 Claim, 2 Drawing Sheets

SYSTEM FOR MEASURING VIBRATIONS OCCURING ON A SURFACE

This application is a divisional of pending prior U.S. patent application Ser. No. 12/902,571 filed on Oct. 12, 2010 entitled "Laser Based Acousto-Optic Sensing Enhancement Using Tailored Retro-Reflectors". This application claims the benefit of the prior application's filing date.

STATEMENT OF GOVERNMENT INTEREST

The invention described herein may be manufactured and used by or for the Government of the United States of America for Governmental purposes without the payment of any royalties thereon or therefore.

CROSS REFERENCE TO OTHER PATENT APPLICATIONS

None.

BACKGROUND OF THE INVENTION (1) Field of the Invention

The present invention is directed to a sensing and tracking system and method of use for enhancing laser based acousto-optic sensing with the sensing and tracking system employing tailored retro-reflector devices. The retro-reflector devices amplify acoustics sensed in particular frequency bands as a function of an acoustic incidence angle and a laser beam interrogation angle. The sensing and tracking system searches for optical reflections or glints from one or more deployed retro-reflector devices in order to measure surface vibrations of the devices. The surface vibrations are caused by the amplified acoustics of an underwater sound source incident upon the devices.

2) Description of the Prior Art

A laser Doppler vibrometer (LDV) is a commonly-known device which is capable of directing a single output laser beam onto a measuring surface in which surface vibrations are measured when the laser beam is reflected back from the measurement surface into the LDV. Interference between the output laser beam and the reflected beam provides a measurement of the velocity and displacement of the surface. This action is useful for measuring surface vibrations produced by pressure waves from an underwater source.

However, reflections from a water surface tend to be weak, sporadic, and thus difficult to detect. A surface with poor reflective quality, turbulence, a high sea state or a foamy condition degrades sensor performance by deflecting the laser beam away from the detector; thereby, increasing signal dropout. One remedy is to monitor the water surface glint locations and to continually steer the laser beam onto an optical glint—such as a naturally direct reflecting point on the unaided water surface.

Glint detection is accomplished by directing a laser at the water surface; identifying areas of direct reflection back to the source; obtaining an image of these temporally and spatially varying laser glint positions using a photosensor array; and steering the beam into the glint location on the water surface. In a real world example, laser based tracking systems are employed during eye surgery to accommodate eye movement during the operation.

A combined LDV and tracker system finds the points where reflection will occur by employing a complex algorithm to continually steer the light beam of the tracker in order to maintain sight of the dynamic reflection point on the water surface. An issue with this system is that natural water surface glints depend on sea state wave slopes and predominantly occur at a nadir+/−20°. This limits the angles at which the laser can be employed to probe the water surface.

Since the water surface acts as a specular reflector, the output laser of the LDV must be perpendicularly incident to the water surface in order to acquire a reflected beam. In normal operating situations, turbulent and hydrodynamic conditions prevail; thereby, resulting in significant intermittence of a received optical signal.

Intermittence of signal detection occurs when the slope of the wave surface changes with respect to the incident laser beam angle. The most troublesome problem governing LDV performance on moving reflective surfaces is signal dropout. In such a situation, it is difficult for the sensor system to capture the reflected beam.

Another problem is the poor reflective quality of the surface. One remedy is to illuminate the surface and to track the reflections. Image-based tracking using an array of photosensors finds points where the required reflection will occur in the tracker which seeks to find the point of reflection and which relies on complicated algorithms to steer the laser beam onto this dynamic point.

Natural water reflections or glint points that are identified by an illuminating source, predominantly occur at the nadir+/−20°. This occurrence limits the angles that the laser output beam may probe the water surface. Also, glint features on the water surface tend to be temporarily and spatially indeterminate which also makes continuous tracking difficult.

An example of a system for tracking glints is disclosed in U.S. Pat. No. 7,251,196, (Antonelli et. al.) and is commonly assigned to the assignee herein. The teachings of U.S. Pat. No. 7,251,196 are incorporated herein by reference.

The Antonelli reference discloses a passive acoustic sensor to detect underwater sounds by using optics in order to determine vibration on the unaided surface. The tracking system must produce a light beam that is perpendicularly incident to the water surface. This positioning reduces the angular approaches that are available for tracking.

In addition, the turbulent and hydrodynamic wave conditions that often prevail under normal situations cause the slope of the turbulent wave surface to rapidly change. Accordingly, significant intermittence or signal dropout of the optical signal reflected from the water surface is expected as the slope changes relative to the incident angle of the laser beam.

A known laser-pumped acoustic sensor system is disclosed in U.S. Pat. No. 7,113,447 (Matthews et al.) and assigned to the assignee herein. The teachings of U.S. Pat. No. 7,113,447 are incorporated herein by reference. The system of the cited reference discloses a laser-pumped compact acoustic sensor system, wherein one or more hollow spherical shells vibrate in response to impinging acoustic signals. The shells have one or more portions that are reflective of impinging laser radiation. A resilient matrix, in contact with the water, supports the shell.

Further, in the cited reference, a laser Doppler velocimeter transmits radiation onto the reflective portion of the shell and receives reflected radiation therefrom. The reflected radiation produces signals in the laser Doppler velocimeter that claim to be representative of acoustic signals in the water. A computer, responsive to the signals, produces a display representative of direction and range to a target.

Known optical sensor systems rely on reflections from a reflecting object. However, the reflections are not directional; meaning that the diffuse reflections reflect energy in all directions and only a small portion of the reflected energy is detected. Accordingly, these systems are susceptible to background light noise; thereby, resulting in reduced reliability.

There is therefore a need for a system to amplify, locate, track and detect laser reflections with increased temporal and spatial resolution. Such a system should be able to track and detect reflections over broader interrogation angles; detect reflections with reduced or no significant signal dropout; and increase the signal strength of reflected signals.

SUMMARY OF THE INVENTION

The present invention generally relates to the use of and supporting system for a retro-reflective device deployable on a water surface. The retro-reflective device is capable of reflecting a beam of laser radiation back to a source along the incident beam angle. The retro-reflector device amplifies resonant vibrations imparted thereto by pressure waves emanating from an underwater source of acoustic radiation (ie: a target).

The retro-reflector device is employable with the supporting system for tracking and detecting tracking optical beam reflections or glints of a tracking beam directed towards a field having one or more retro-reflector devices. By use of the retro-reflector device, the glints are sustainable through changing wave slope conditions; thereby, facilitating tracking and reducing signal dropout of laser reflections. The reflected laser radiation is combined in an interferometer with the reference beam to determine the amplitude and frequency of the surface velocity and displacement due to the underwater source of acoustic radiation.

The retro-reflector device comprises a shell having physical properties for controlling a characteristic spatial and spectral response to acoustic signals. Physical properties of the shell include a thickness, radius and material composition which are chosen to affect spatial, resonance, and spectral response of acoustic signals. The resonant vibration frequency of a hollow, spherical device occurs when the shell diameter is half of the acoustic wavelength.

According to one embodiment of the invention; the retro-reflector device comprises an evacuated rigid shell (such as a sphere or cylinder). The shell exhibits a resonance such that a free field surface velocity of the retro-reflector device is greater than twice the particle velocity of the water by the condition that the water-to-retro-reflector boundary constitutes a pressure release surface.

A spherical retro-reflector device having a selected thickness, radius and material composition can amplify impinging acoustic signals by vibrating at or near its resonant frequency. The resonant vibration amplitude is distributed spatially along the outer surface of the retro-reflecting sphere. Therefore, the measured vibration amplitude will vary as a function of an acoustic incidence angle distributed spatially across the outer surface of the retro-reflecting sphere device. Therefore, the measured vibration amplitude will vary as a function of an acoustic incidence angle distributed spatially across the outer surface.

The retro-reflector device has at least one frequency resonant acoustic response greater than an incident plane wave velocity that is specific to the spherical device dimensions; a spatially-distributed response on the outer surface from an acoustic incidence angle selective response due to constructive and destructive interference of the device's surface vibrations. As such, the measured vibration amplitude may vary as a function of the interrogation beam angle.

The retro-reflector device includes one or more retro-reflecting surfaces with approximately one hundred percent reflectivity. The retro-reflectivity is in a range of the nadir+/− 90°. The retro-reflector device also enables a sustainable glint for as long a duration as is visible to the tracker system and laser interferometer interrogation beam.

The retro-reflector device has a deterministic shape, such as hollow sphere, for enhancing temporal and spatial trackability; and produces a minimum detectable signal at least greater than that of a free surface.

The retro-reflector device has a free field surface velocity greater than two times the in-water particle velocity and is governed by one or more of: a resonant frequency, $f^n_{res}$, wherein "n" is at least one; a shell damping loss factor "$\epsilon$" of approximately "j" mod elasticity/real mod elasticity governing peak $V_{amp}$ and sharpness of resonance frequency, and where $\epsilon$ is inversely proportional to $V_{amp}$ and is directly proportional to resonance width.

The retro-reflector device has a $f^{sub}_{res} <= f^{float}_{res} </= f^{vac}_{res}$, where: $f^{vac}_{res}$ is invacuo resonance; $f^{sub}_{res}$ is fully-submerged resonance; and $f^{float}_{res}$ is one half of submerged resonance for the device. Estimated solutions for $f^{sub}_{res}$; $f^{float}_{res}$; and $f^{vac}_{res}$ are governed by an expression $f^{sub}_{res} \approx (f^{vac}_{res} + f^{sub}_{res})/2$.

In another embodiment, the invention comprises a system for measuring vibrations occurring on a surface having at least one retro-reflective device; a glint tracker for producing a scanning tracking beam on an axis in order to locate the retro-reflector device; and a detector responsive to reflected glints along the axis from the retro-reflector device in order to establish a directional location thereof.

The system also comprises a laser interferometer (such as a laser Doppler vibrometer) for producing a coherent laser interrogation signal along the axis of the tracking beam directed at the retro-reflector device and for being responsive to detect reflections of the interrogation signal from the retro-reflector device in order to enable continuous measurement of surface vibrations thereof.

In yet another embodiment, the invention is directed to a method for measuring acoustic vibrations occurring on a surface with the method comprising the steps of: deploying one or more retro-reflective devices onto the water surface; producing a tracking beam on an axis; detecting reflected tracking beam radiation from the retro-reflector devices along the axis; establishing a directional location; directing a coherent laser interrogation signal along the axis of the tracking beam; detecting reflections of the interrogation signal from the retro-reflector devices; and measuring surface vibrations of the retro-reflector devices based on the reflections.

DESCRIPTION OF THE INVENTION

Figure 1:
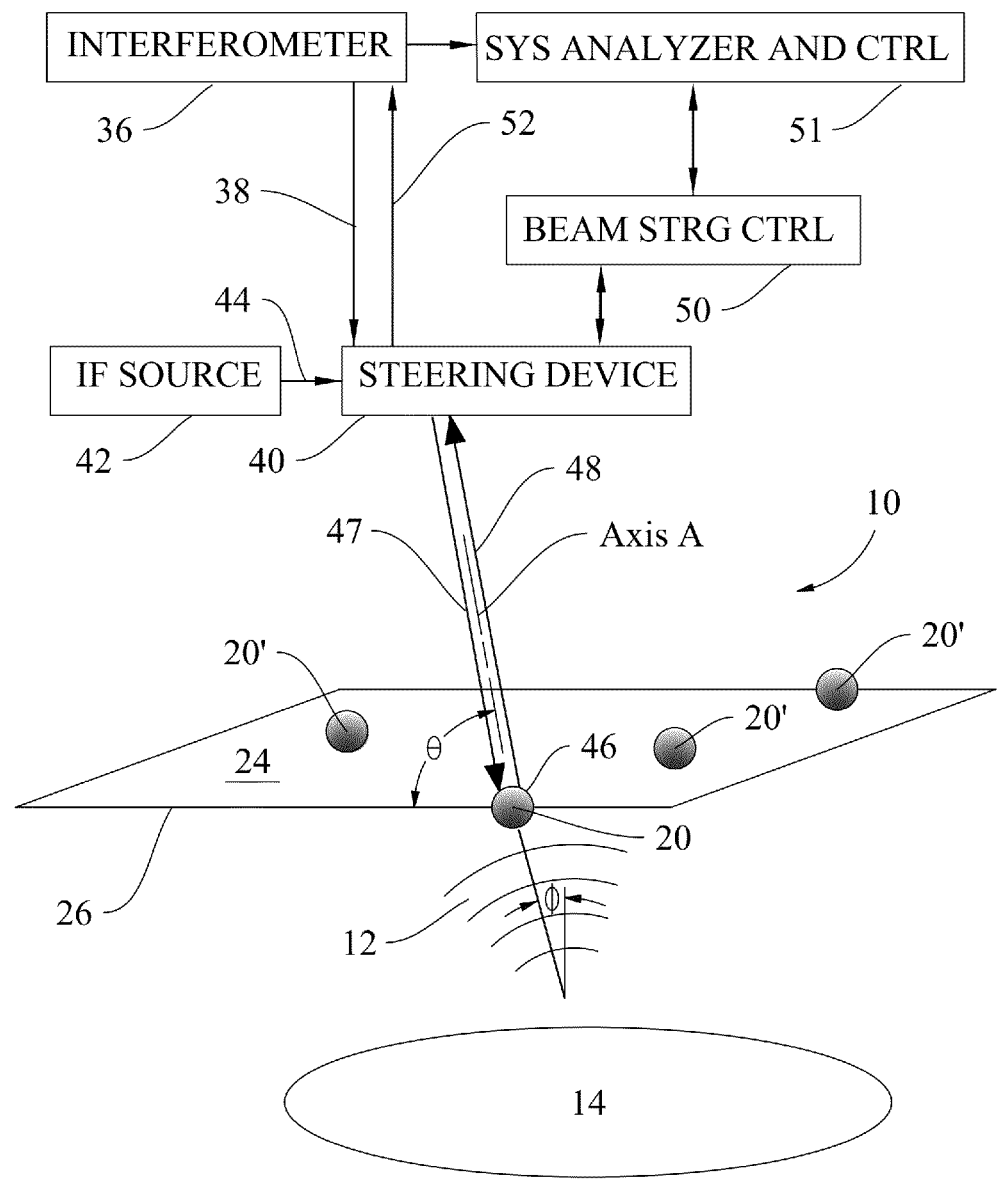
FIG. 1 is a schematic illustrating an arrangement of the present invention.

FIG. 1 illustrates a system 10 of the present invention in which the system is capable of detecting acoustic signals 12 produced by an undersea sound source 14. In operation, the acoustic pressure waves generated by the sound source 14 impinge on retro-reflector devices 20 deployed over a search field 24 and floating on an ocean surface 26. The retro-reflector devices 20 are capable of vibrating in response to the impinging pressure waves of the acoustic signals 12.

A laser interferometer 36 produces an output interrogation beam 38 that is directed to a beam steering device 40.

The interferometer 36 may be any one of a variety of suitable devices known in the art for measuring the change in the optical characteristic of the interrogation beam reflected from the retro-reflector device 20. In the exemplary embodiment, the interferometer 36 illustrated is a laser Doppler vibrometer (LDV).

An infrared (IF) source 42 produces a tracking beam 44 which is directed to the steering device 40. The interrogation beam 38 and the tracking beam 44 are superimposed on each other in the steering device 40. The steering device 40 then transmits the combined laser interrogation beam and tracking beam along a beam axis "A", at an interrogation angle θ towards the targeted retro-reflector device 20.

The retro-reflector devices 20, 20' amplify the pressure waves impinging thereon from the sound source 14 by producing resonance vibrations in a particular frequency range on an outer surface 46 of the device. The magnitude of the detected vibrations is a function of the acoustic sound pressure level, the acoustic incidence angle θ and the wavelength of the laser interrogation beam 38.

The retro-reflector device 20 is characterized by the ability to reflect an incident optical beam back toward its source. Retro-reflector materials include any material that has retro-reflective capability. In the exemplary embodiment, the retro-reflector device 20 is a hollow brass sphere having a retro-reflective outer surface coating. Surface treatments include paint, tape and the like in which the treatments have retro-reflective properties.

In the present arrangement, a combined interrogation and tracking beam (hereinafter "47" as the combined beam) are reflected back towards the steering device 40.

The reflected tracking beam (hereinafter called glint 48) is sensed by a photo-detector contained within a beam steering controller system 50 which senses glints from the retro-reflector device 20 and controls the steering mirrors within the beam steering device 40 in order to continuously track the position of the retro-reflector device. The steering device 40 is capable of steering the optical axis "A" of the combined interrogation and tracking beam 47 to follow the retro-reflector device 20 that is being tracked.

The combined interrogation and beam 47 is reflected back from the retro-reflector device 20 back towards the steering device 40 and is thereafter directed along an optical path 52 to an input of the interferometer 36. The reflected interrogation beam is directed onto the photo-sensor within the interferometer 36 along with a reference laser beam contained within the interferometer system to produce a signal indicative of the velocity of the amplified vibrations produced by the retro-reflector device 20. This signal is an indicator of the amplitude and frequency of the underwater sound source 14.

When the combined beam 47 is directed at two or more retro-reflector devices 20' to detect a target signal; the signals may be employed to provide a more accurate position of the underwater sound source 14 using traditional beamforming analysis combined with knowledge of the steering angle of the axis "A" of the beam steering device 40.

The combined beam 47 is scanned over the search field 24 by the steering device 40 and searches for glints from the retro-reflector devices 20, 20'. Detected glints are then tracked by the steering control 50 and the steering device 40 to direct the beam 47 to illuminate the retro-reflector devices 20, 20' and returns the reflected interrogation beam contained in 48 to the interferometer 36 via the steering device 40 and the optical path 52.

The reflected interrogation beam on the optical path 52 is combined with a reference laser beam within the interferometer 36 to produce amplified outputs indicative of the acoustic pressure waves. A measurement of the amplitude and frequency of the surface is obtained from which the position of the underwater sound source 14 is derived within a system analyzer and controller 51. The system analyzer and controller 51 obtains the voltage output from the interferometer 36 and the steering angle from the tracking controller 50. The system analyzer and controller 51 calculates the sound source signal amplitude and frequency content including the vibration velocity and displacement and location.

The tracking feature allows the superimposed interrogation beam 47 to closely follow the retro-reflector device 20 whereby continuous measurement of the reflected signals may be obtained with high resolution and little or no signal dropout.

Naturally-occurring glints are temporally unstable and tend to quickly disappear within approximately one millisecond—depending on the sea state conditions. As a result, the tracker must acquire a new glint. The retro-reflector device 20 provides a more sustainable glint that can be efficiently and sustainably probed with the laser beam.

As previously noted, the foremost issue governing acousto-optic sensor performance on moving reflective surfaces is signal dropout due to laser reflections not being captured by the sensor system or beam detector. Optical dropout that is prevalent with conventional systems is drastically reduced because the retro-reflector device 20 can float on the water surface; can self-right itself and can provide a stable, wide angle reflection of the interrogation and tracking beams at oblique and normal incidence. The ability of the retro-reflector device 20 to reflect back along the same optical path as the source, allows for a widened range of laser probe angles which can greatly reduce signal dropout.

The retro-reflector device 20 described herein moves on the water surface in a more determinable and predictable way as compared with a glint feature from a natural or an unaided water surface. The retro-reflector device 20 also has a deterministic shape that is easily recognized and is readily trackable temporally and spatially than in an image-based, laser glint tracking system—operating on an unaided ocean surface.

The retro-reflector device 20 can resonate in order to amplify the acoustic vibrations impinging on the device; thereby, presenting a stronger signal for detection. Specific features are designed into the retro-reflector device 20 to increase sensitivity within certain acoustic frequency bands as a function of the acoustic incidence angle and laser beam interrogation angle.

The minimum detectable signal level as well as detection sensitivity are increased by several orders of magnitude. The combination of the interferometer 36 with distributed retro-reflector devices 20 results in an improved system with enhanced performance.

A tracking and detection system according to the present invention employs retro-reflector devices; a laser interferometer; and a glint tracking system. In operation, the interferometer produces an output beam directed along a steerable beam axis. The output beam is directed to one or more locations of the retro-reflector devices distributed in a search field on the ocean surface.

A continuous wave (CW) laser source or tracking beam is used to scan the surface in order to locate a glint location and to direct the interrogation beam 47 at the retro-reflector device 20 in order to detect the reflected light containing information of the amplified acoustic response of the retro-reflector device.

The interrogation beam 38 is superimposed on the tracking beam 44 and is steered by the steering device 40 to continually track reflected glints from the retro-reflector devices 20 so that signal dropout is reduced or eliminated.

Figure 2:
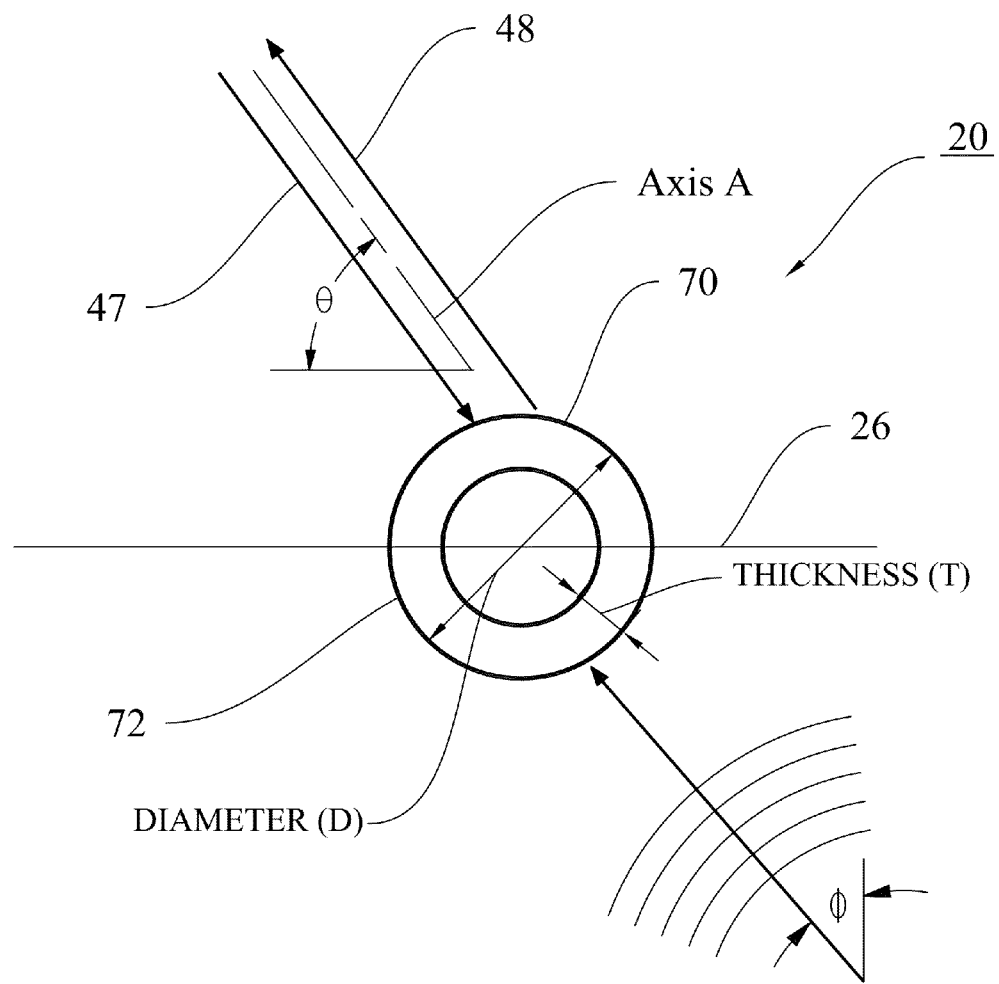
FIG. 2 is an illustration of the use of a retro-reflector device according to the present invention.

An exemplary retro-reflector device 20 is illustrated in FIG. 2. In the figure, the retro-reflector device 20 comprises an evacuated brass sphere having a diameter "D" of approximately 1.5-5 inches and a wall thickness "T" of approximately 1.5 inches. The retro-reflector device 20 may also be cylindrical or any other suitable shape.

The retro-reflector device 20 may be formed of other metals and non-metals (such as plastics and ceramics) having suitable resonance properties for amplifying the acoustic vibrations impinging from sub-surface acoustic sources.

The retro-reflector device 20 in FIG. 2 is depicted as a half-submerged sphere on the ocean surface 26. The retro-reflector device 20 has an in-air section 70 and an in-water section 72. The parameter choices control the spatial and spectral magnitude (i.e., amplification, structure of the acoustic resonance properties) of the exposed in-air section 70 which are a function of the acoustic angle of incidence Φ of an incident acoustic wave (incident plane wave). In operation, the combined beam 47 probes the retro-reflector device 20 along the axis "A" and receives a reflected beam from the in-air section 70 along the same axis.

For a half-submerged floating elastic shell, an incident acoustic wave 12 having a particle velocity $V_{INC}$ that is impinging on the in-water section 72 is amplified. With no retro-reflector device 20 present, the free field surface particle velocity $V_{SURFACE}$ is double the incident particle velocity (i.e., $V_{SURFACE} = 2V_{INC}$).

The floating retro-reflector device 20 excites a resonance of the shell in order to magnify the velocity of a dry shell above the $2V_{INC}$ level so that an acousto-optic sensor can more easily sense the signal carried by the beam 38 reflected from the exposed upper in-air section 70.

It is generally desirable for the shell to amplify the incident plane wave velocity $V_{INC}$. In an exemplary embodiment, it is desired that the shell meet the criterion: $V_{amp} = V_{shell}/V_{INC} \gg 2$ for amplification of an incident acoustic pressure wave.

Exact analytical solutions are not currently available for cylindrical and spherical shaped models to define conditions under which significant floating shell velocity amplification, $V_{INC} \gg 2$. However, simplifying assumptions may be employed to establish a boundary on determining the potential magnitudes of $V_{amp}$ and importantly, at which incident wave frequencies $f_{res}$ where these amplifications can be expected.

Simulations of a submerged spherical retro-reflective shell show that a substantial amplification of $V_{INC}$ greater than two can be achieved by synthesizing the retro-reflective shell to have resonant frequency $f''_{res}$ values corresponding to a low number of mode shape lobes (n=number of lobes).

Shell damping or loss factor, (H=ratio of complex-to-real modulus of elasticity) governs the peak velocity amplification $V_{amp}$ and the sharpness of the resonance in frequency. A smaller eta provides a bigger $V_{amp}$ amplification (a desirable feature), but narrower shaped resonance plots (an undesirable circumstance). Conversely, a bigger eta reduces amplification which is undesirable, but widens the resonance plots which is desirable.

In the case of an exemplary half-submerged floating spherical shell retro-reflector device, the values of resonant sphere frequencies $f^{float}_{res}$ (floating sphere resonance) for a particular mode shape is bounded by the expression: $f^{sub}_{res}$ (fully submerged resonance) $</= f^{float}_{res} </= f^{vac}_{res}$ (invacuo resonance).

Analytical solutions exist for the invacuo resonance and the fully submerged resonance. Estimates exist for half-submerged resonance as follows: $f^{sub}_{res} \approx (f^{vac}_{res} + f^{sub}_{res})/2$.

In an example, a finite element model for a floating cylinder was employed to determine the response of floating objects with a circular cross-section. The model is affected by water impedance loading of the half-submerged portion of the model. The model determines if averaging approximation works when the actual solution is known as a reference; and whether deformation and velocity shapes are affected by non-normal incidence.

Two half-submerged cylinder resonant models were simulated and computed with a Finite Element Method (FEM) and compared against an approximate averaging formula where n=4 lobe mode: $f^{float}_{res} = 23.3$ using FEM & $f^{float}_{res} = 22.7$ with averaging. N=G lobe mode: $f^{float}_{res} = 59.1$ using FEM & $f^{float}_{res} = 59.7$ with averaging.

The half-submerged cylinder was loaded with a plane wave input at four different acoustic angles of incidence. Substantial shell velocities were experienced at off normal acoustic incidence, and different parts of the in-air portion have peak velocities that depend on the acoustic plane wave velocity.

The results achieved with exemplary retro-reflector devices indicate that the design of the mechanical properties provides a way to magnify the acousto-optic response of the retro-reflector device; thereby, effectively increasing the overall acousto-optic sensitivity. The design of the retro-reflector device 20 can enhance certain particular frequency components while suppressing other components. The response of a retro-reflector device 20 as a function of acoustic incidence angle may be employed to add yet another capability.

The combination of an LDV with tracking and retro-reflector properties enhances detection capabilities; thereby, maintaining a continuous laser reflection back to the interferometer 36 from the retro-reflector measurement surface at any angle of interrogation.

The acousto-optic sensor described herein is capable of measuring vibrations of surfaces with high speed variations of the temporal and spatial deterministic retro-reflective surfaces in motion at a slower rate than the corresponding water surface.

The use of the retro-reflector device described herein provides standoff detection in instances where the acousto-optic sensing system is at low altitudes because laser-induced glints on the unaided water surface are mainly confined to +/−20° of normal incidence.

The invention employs an interferometer but is not limited to any particular design type. It is believed that the described methodology for finding a useful design is sufficient to enable one of ordinary skill in the art to find a useful design for a particular application.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method for measuring acoustic vibrations occurring on a water surface, said method comprising the steps of:
   providing at least one retro-reflector device with the at least one retro-reflector device comprising a shell capable of exhibiting a spatial and spectral response to acoustic signals wherein the shell is an evacuated rigid shell having a selected thickness, radius and material composition capable of amplifying impinging acoustic signals as a function of acoustic incidence angle distributed spatially across an outer surface;

deploying the at least one retro-reflector device onto the water surface;
producing a tracking beam on an axis with a glint tracker;
directing the tracking beam on the water surface toward a field having the at least one retro-reflector device;
detecting reflected glints from the retro-reflector device along the axis for establishing a directional location;
superimposing a laser interrogation signal along the axis of the tracking beam toward the retro-reflector device;
detecting reflections of the interrogation signal from the retro-reflector device, with said detecting step provided by a detector;
interfering with a laser interferometer, a reference signal corresponding to the interrogation signal and the reflections from the retro-reflector device;
measuring surface vibrations using the reference signal and the laser interferometer to extract at least one of a surface vibration amplitude, surface vibration frequency, surface vibration velocity and surface vibration displacement.

* * * * *